(12) United States Patent
Wang et al.

(10) Patent No.: US 10,647,659 B2
(45) Date of Patent: May 12, 2020

(54) PROCESS FOR PRODUCTIONS OF FORMAMIDES AND ACRYLAMIDES

(71) Applicant: SHENZHEN UV-CHEM TECH INC, Shenzhen (CN)

(72) Inventors: Zhigang Wang, Shenzhen (CN); Haoyu Ding, Shenzhen (CN); Langxi Hu, Shenzhen (CN)

(73) Assignee: Shenzhen Youwei Technology Holdings Group CO., LTD., Shenzhen (CN)

( * ) Notice: Subject to any disclaimer, the term of this patent is extended or adjusted under 35 U.S.C. 154(b) by 0 days.

(21) Appl. No.: 16/656,425

(22) Filed: Oct. 17, 2019

(65) Prior Publication Data
US 2020/0048186 A1 Feb. 13, 2020

Related U.S. Application Data

(63) Continuation of application No. PCT/CN2018/087132, filed on May 16, 2018.

(51) Int. Cl.
| | | |
|---|---|---|
| C07C 231/12 | (2006.01) |
| C07C 231/02 | (2006.01) |
| C07C 231/10 | (2006.01) |
| C07C 233/20 | (2006.01) |
| C07C 233/31 | (2006.01) |
| C07C 233/47 | (2006.01) |
| C07C 233/78 | (2006.01) |
| C07D 265/30 | (2006.01) |
| C07D 295/18 | (2006.01) |

(52) U.S. Cl.
CPC .......... *C07C 231/12* (2013.01); *C07C 231/02* (2013.01); *C07C 231/10* (2013.01); *C07C 233/20* (2013.01); *C07C 233/31* (2013.01); *C07C 233/47* (2013.01); *C07C 233/78* (2013.01); *C07D 265/30* (2013.01); *C07D 295/18* (2013.01)

(58) Field of Classification Search
None
See application file for complete search history.

(56) References Cited

U.S. PATENT DOCUMENTS

2018/0030009 A1* 2/2018 Ding ................. B01J 31/24

* cited by examiner

*Primary Examiner* — Sudhakar Katakam
*Assistant Examiner* — Jennifer C Sawyer
(74) *Attorney, Agent, or Firm* — CBM Patent Consulting, LLC

(57) ABSTRACT

This invention relates to performance chemicals field, it discloses a novel and green process for simultaneous productions of formamides as well as mono- and multi-functional acrylamides under very mild conditions and with high efficiency. These substances are widely useful as industrial solvents or raw materials, in particular acrylamides are important olefinically-unsaturated polymerizable monomers in photo-curing materials.

16 Claims, No Drawings

PROCESS FOR PRODUCTIONS OF FORMAMIDES AND ACRYLAMIDES

This application claims priority to PCT international application number PCT/CN2018/087132 filed on 16 May 2018 and Chinese application CN 201710376213.8 filed on 18 May 2017.

FIELD OF THE INVENTION

This invention relates to performance chemicals field, it discloses a novel and green process for simultaneous productions of formamides as well as mono- and multi-functional acrylamides under very mild conditions and with high efficiency. These substances are widely useful as industrial solvents as well as raw materials, in particular acrylamides are increasingly important olefinically-unsaturated polymerizable monomers in photo-curing materials.

BACKGROUND

Mono- and multi-functional acrylamides are important olefinically-unsaturated polymerizable monomers in photo-curing materials. They display several significant merits as compared to such more conventional monomers as acrylates or styrenes. For one, they typically demonstrate significantly higher polymerization reactivities than acrylate-type monomers bearing equal functionalities; two, they usually have much improved biological safeties and compatibilities, particularly in terms of odor as well as physiological skin irritation profiles, which would be critical for biomedical applications as well as on-site applications involving human occupants; three, they have robust solubility properties that are often conducive for both solvent-borne as well as water-borne formulations; four, they often feature low viscosities, which is highly desirable for formulating high-solid-content as well as solventless sprayable coats and inks with no or reduced emissions of VOCs (i.e., Volatile Organic Compounds). These technical advantages collectively hold promises for more market growths for acrylamides materials.

Furthermore, it is known to experts skilled in the art that, unlike the preparations of acrylates where direct esterifications are feasible through the reactions of acrylic acids and alcohols precursors, acrylamides can not be prepared in otherwise similar processes from acrylic acids and amines since the latter would inevitably incur so-called Michael addition by-products. There are thus up to date fairly limited disclosures in the literature on the preparation methods for acrylamides. Few know protocols are Japanese patents JP 09-279395, JP 49-66625, JP 05-163279, PCT filing WO 2015/146876, Chinese patent CN103992294, and scholarly articles *Tetrahedron Lett.* 2003, 44, 7485; *Shan Dong Hua Gong*, 2015, 44, 33; *Ying Yong Hua Gong*, 2015, 44, 1257; *Can. J. Chem.* 1976, 266.

These known disclosures feature either such harsh and operationally challenging conditions as high-temperature thermal cracking technique, or with low production efficiency as well as high capital investments. To date only the Japanese maker, Konjin Chem, has demonstrated commercial production capacities for such hallmark products as 4-acryloylmorpholine (ACMO) and a few other analogs. The Konjin process, however, still employs energy-intensive chemical pyrolysis at temperatures as high as 380° C.

On the other hand, various formamides are widely used as industrial solvents, raw materials, and high-performance electro-chemicals. It is equally notable to people skilled in the art that formamides are not routinely prepared by the direct actions of formic acid and amines (*He Cheng Hua Xue*, 2014, 22, 250). Some relevant literatures on preparations of these substances are Chinese patents CN 2012104656754, CN 2013105013840, CN 2013104152600, and WO 2016131371A. These protocols teach the uses of corrosive halogenated precursors and expensive metal catalysts.

It is thus transparent to the practitioners in the fields that newly inventive production techniques for acrylamides as well as formamides are highly sought-after in order to meet market demands with better operational safety and efficiency, higher levels of environmental friendliness, and above all lower capital investments and cost. The present invention disclosed for the first time a process that can simultaneously produce both types of substances with the above-defined principles.

SUMMARY

The present invention has surprisingly found that, as described in the following equation (I), a range of acrylamides structured as C and formamides structured as D may be simultaneously prepared by the reactions of starting substances structured as A and B, respectively, under the said conditions.

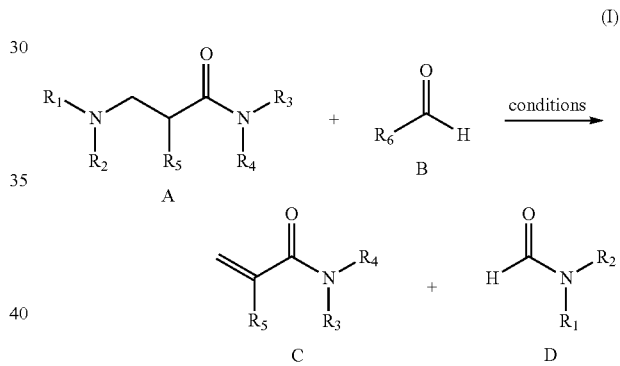

(I)

In equation (I), $R_1$ and $R_2$ is each independently hydrogen, linear or branched aliphatic groups containing 1-24 carbons (hereafter abbreviated as $C^1$-$C^{24}$), the said groups may be interrupted by 1-6 non-continuous O, N, S, F, Si, Si—O, carbonyl, OH, NH, $NH_2$, $CO_2H$, double bond, triple bond, or $C^6$-$C^{24}$ aromatic ring; or, $R_1$ and $R_2$ is each independently $C^6$-$C^{24}$ aromatic groups, the said groups may be substituted by 0-4 $C^1$-$C^{24}$ alkyls, O—$C^1$-$C^{24}$ alkyls, S—$C^1$-$C^{24}$ alkyls, NH—$C^1$-$C^{24}$ alkyls, N—($C^1$-$C^{24}$ alkyls)$_2$, halogens; or, $R_1$ and $R_2$ can also form a $C^3$-$C^{12}$ ring structure, where the rings may be interrupted by 1-4 non-continuous O, N, S, carbonyl, or double bond.

$R_3$ and $R_4$ has each independently the same meanings as does $R_1$ or $R_2$;

$R_5$ is hydrogen, methyl ($CH_3$), or hydroxymethyl ($CH_2OH$);

$R_1$ and $R_2$, or/and $R_3$ and $R_4$, may form a ring structure;

B is a substance bearing a CHO functionality, i.e., B is formic acid, formaldehyde, glyoxal, formates, formamides, ammonium formate, formic acid metal salts, $C^1$-$C^{24}$ aliphatic aldehydes, or $C^6$-$C^{24}$ aromatic aldehydes; Correspondingly, $R_6$ in structure B is H, OH, CHO, $R_1$, $OR_1$, $NHR_1$, $NR_1R_2$, OM (where M is metal or metal cation); When $R_6$=H (i.e., B is formaldehyde), B may be free formaldehyde or any of its associated or polymerized forms, including both solids or liquids states of these forms (the corresponding D is thus $R_1R_2NCH_2OH$).

Preferably $R_6=OH$, i.e., B is formic acid. The said formic acid may be available from commercial sources, or, may be formed in-situ in the relevant reactions. Examples are that contacting formic acid salts with suitable acids to generate in-situ free formic acids. When B is formic acid, as shown in equation (II), the only by-product is water, making the inventive process particularly environmentally green and economically cost-effective.

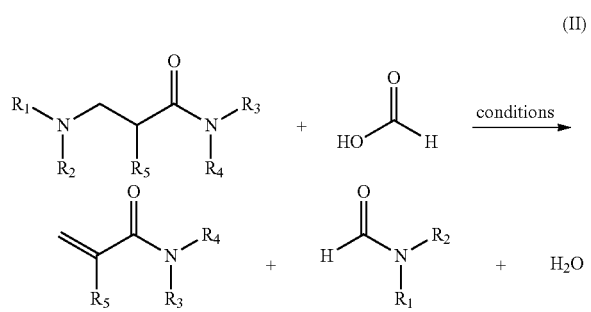

(II)

The said conditions herein denote organic bases, inorganic bases, catalysts, promoters, inhibitors, heat, microwaves, ultrasonic waves, vacuums, pressures, or solvents; or, conditions are any combined uses of any two or more than two of these factors; the said organic bases are aliphatic or aromatic amines; the said inorganic bases are alkaline metals, alkaline-earth metals, or hydroxides, oxides, sulfides, carbonates, carboxylates, sulfonates of transition metals; the said catalysts or promoters are Lewis acidic or basic compounds. The inventive processes preferably employ polymerization inhibitors, the said inhibitors are phenols, phenol derivatives, hydroquinones, benzoquinones, naphthoquinones, phenothiazines, phosphites, N-nitroso-N-phenylhydroxylamine aluminum salt, 4-hydroxy-2,2,6,6-tetramethyl-piperidinooxy, tri-(4-hydroxy-TEMPO) phosphates, copper chloride, copper dibuthyldithiocarbamate, or any combinations of any two or more than two of the above mentioned inhibitors; the amounts of inhibitors employed are in the ranges of 0.01-5% molar fractions (with regard to the reactants), preferably in the ranges of 0.01-3% molar fractions. Heat refers to reaction temperatures, which may range from −25 to 400° C., preferably from 0 to 200° C., more preferably from 10 to 150° C.; Pressure refers to reaction pressure parameters which may range from 0.001 to 50 atm, preferably from 0.001 to 20 atm, more preferably from 0.001 to 10 atm. Solvents may be chosen from aromatic or aliphatic hydrocarbons, halogenated aromatic or aliphatic hydrocarbons, esters, alcohols, ethers, nitriles, ketones, amides, sulfones, carbonates, water, super-critical carbon dioxides, or ionic liquids, or any combinations of any two or more than two of the above mentioned solvents. The uses of solvents are optional but may not always be required, i.e., the processes may be conducted under so-called solvent-less conditions, which is feasible, for example, when the starting materials themselves are liquids at the desired temperatures.

The substances A are often known compounds, and as illustrated in the equation (III), they may either be commercially available or be easily accessed through the sequential condensations between amine E, acrylates F, and amine G (where $R_7$ has the same definition as that of $R_1$), following known literature protocols (for example, *Tetrahedron Lett.* 2008, 49, 5147).

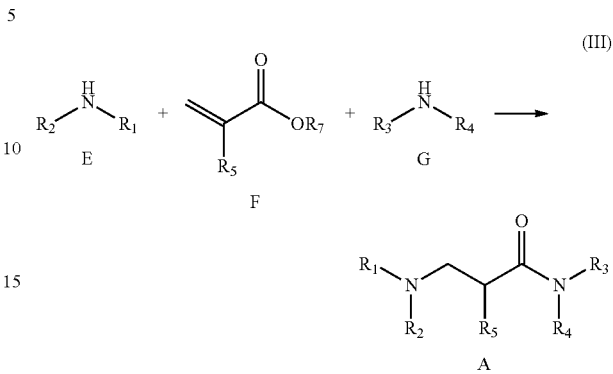

Therefore, the products acrylamides C and formamides D may alternatively be prepared without incurring the isolation or purification of preformed intermediate A; within this scenario, the direct action of the in-situ prepared A with B would furnish the desired products. As such, the combination of equations (III) and (I) readily allows the products to be prepared via a remarkable "one-pot" fashion, enhancing significantly the invention's operational easiness and cost competitiveness.

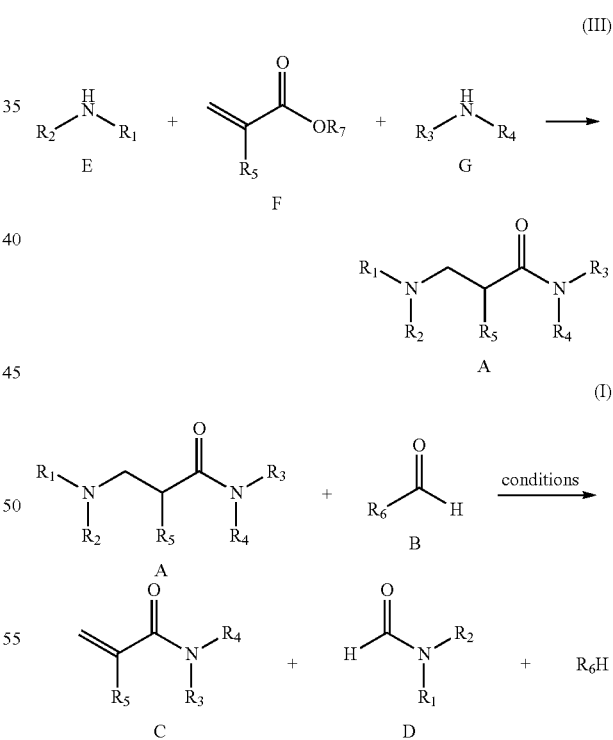

Two illustrative demonstrations of the invention are shown in equations below. The corresponding intermediates A are prepared by following literatures (JP09-279395 and JP2006182676) One discloses the preparations of 4-acryloylmorpholine (known as ACMO) and N-formylmorpholine; the other describes the syntheses of N,N-diethyl acrylamide (known as DEAA) and N,N-diethyl formamide.

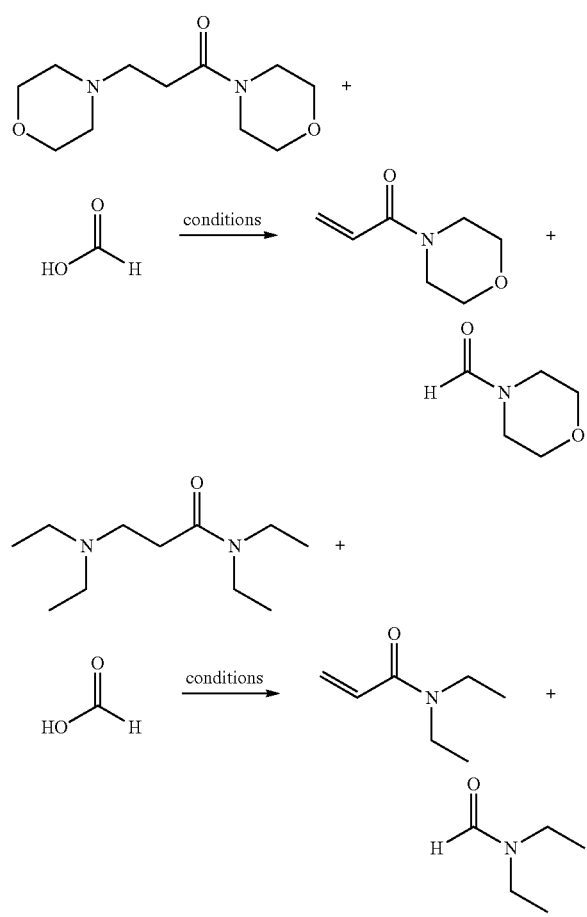
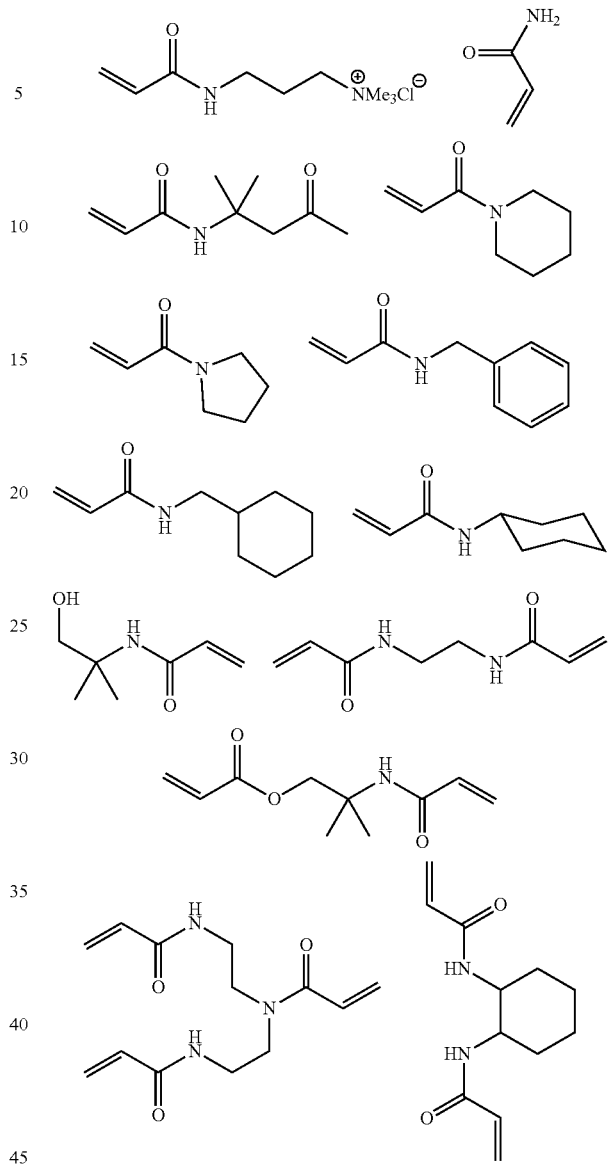
The acrylamides that can be prepared by this invention are summarized below in some illustrative but not limiting structures:
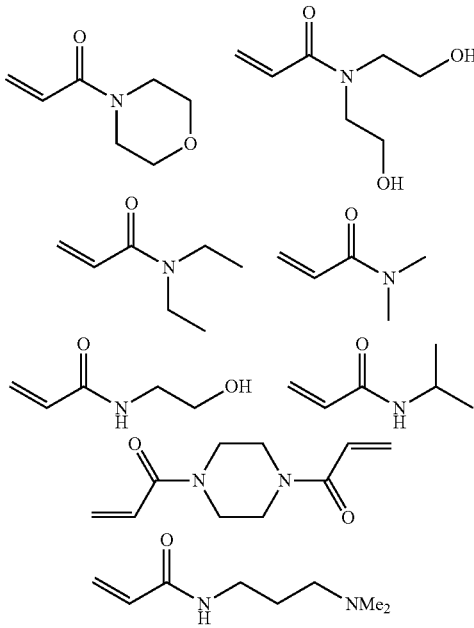
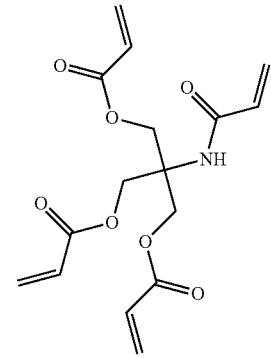 [SMILES: C=CC(=O)NC(COC(=O)C=C)(COC(=O)C=C)COC(=O)C=C]
These acrylamides are important olefinically-unsaturated polymerizable monomers in photo-curing formulation materials. Further experimental details on the invention are disclosed in due course.

DETAILED DESCRIPTION OF THE INVENTION

Experiment 1

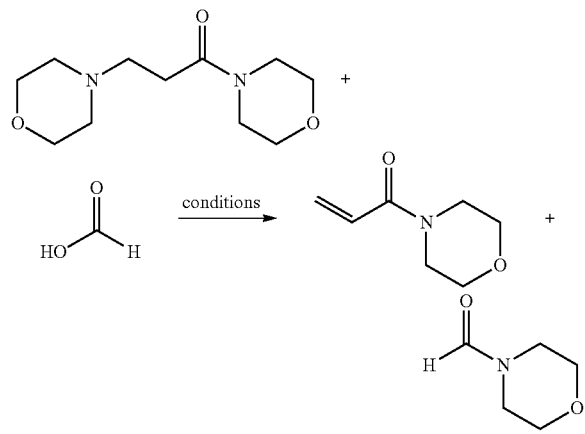

Under Argon atmosphere, a mixture of 50.0 g 1,3-dimorpholinopropan-1-one, 11.1 g formic acid, 0.5 g phenothiazine, and 200 mL xylene was charged into a flask and further heated up to 140° C. with stirring for 2 hrs, an additional portion of 11.0 g formic acid was added and the stirring was continued overnight. The crude mixture was concentrated under reduced pressure to give 45.5 g crude oil. GC analysis on the sample revealed formation of N-formylmorpholine (48.7%) and ACMO (51.8%). Fractional distillation of the crude mixture furnished the two products in pure forms.

Experiment 2

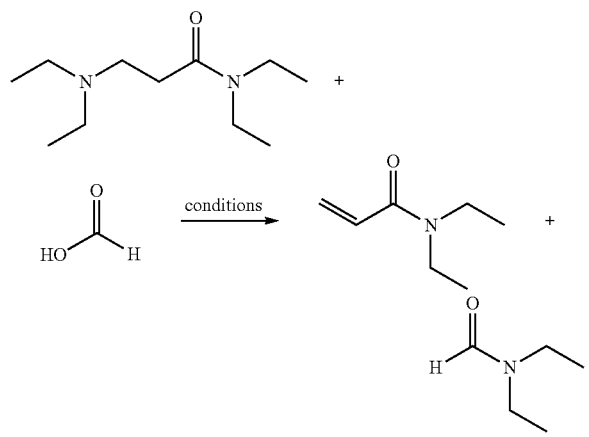

Under Argon atmosphere, a mixture of 40.0 g 3-(diethylamino)-N,N-diethyl-propanamide, 9.2 g formic acid, 0.4 g phenothiazine, and 170 mL xylene was charged into a flask and further heated up to 140° C. with stirring for 2 hrs, an additional portion of 9.2 g formic acid was added and the stirring was continued for 8 hrs. The crude mixture was concentrated under reduced pressure to give 52.6 g crude oil. GC analysis on the sample revealed formation of N,N-diethylformamide (46.7%) and N,N-diethyl acrylamide (49.2%). Fractional distillation of the crude mixture furnished the two products in pure forms.

Experiment 3

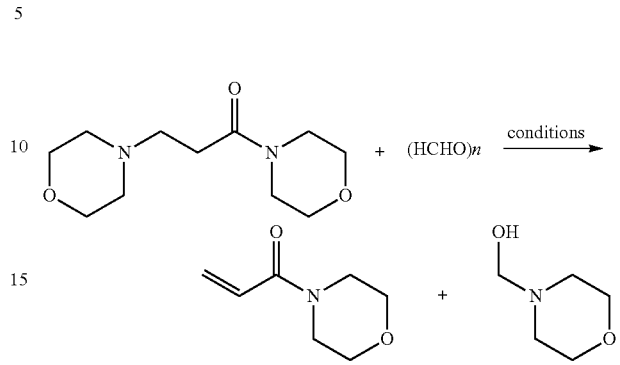

Under Argon atmosphere, a mixture of 50.0 g 1,3-dimorpholinopropan-1-one, 7.2 g paraformaldehyde, 0.5 g phenothiazine, and 200 mL xylene was charged into a flask and further heated up to 110° C. with stirring for 4 hrs, an additional portion of 7.2 g paraformaldehyde was added and the stirring was continued for 8 hrs. The crude mixture was concentrated under reduced pressure to give 42.5 g crude oil. GC analysis on the sample revealed formation of morpholinomethanol (48.9%) and ACMO (52.1%). Fractional distillation of the crude mixture furnished ACMO in pure form.

Experiment 4: One-Pot Synthesis from Acrylic Acid

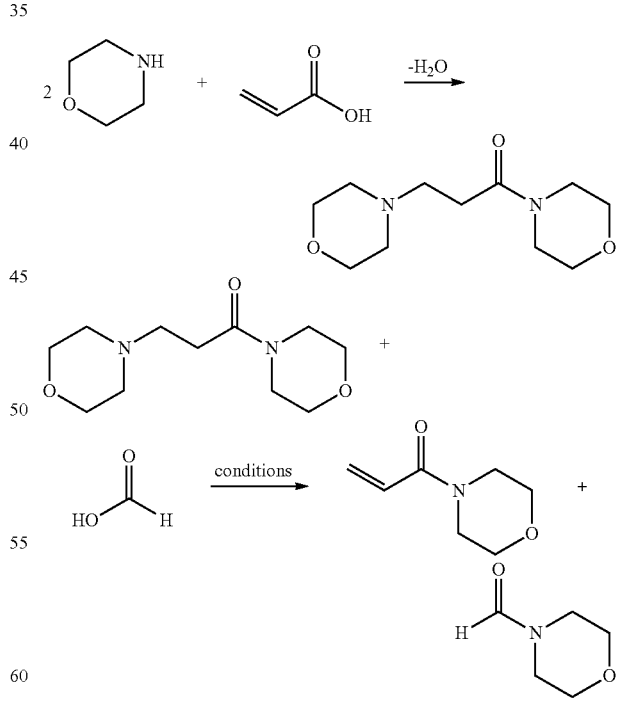

Under Argon atmosphere, a mixture of 322.0 g morpholine and 66.3 g acrylic acid was charged into a flask and heated up to 50° C. with stirring for 0.5 hr. The reaction was further brought to 135° C. for 8 hrs. After the formed morpholine and water were removed under reduced pressure at 100° C., an additional portion of 147.4 g anhydrous morpholine was added. The mixture was heated to 135° C. and refluxed for 3 hrs, on which point the formation of 1,3-dimorpholinopropan-1-one was judged to be complete. Excess morpholine was completely removed by distillation with reduced pressure at 100° C. and further at high vacuum. The formed 203.0 g 1,3-dimorpholinopropan-1-one was directly combined with 45.2 g formic acid, 1.9 g phenothiazine, and 1 L xylene, and the resultant mixture was further heated up to 140° C. with stirring for 4 hrs, an additional portion of 46.2 g formic acid was added and the stirring was continued overnight. The crude mixture was concentrated under reduced pressure to give 198.4 g crude oil. GC analysis on the sample revealed formation of N-formylmorpholine (45.4%) and ACMO (50.6%). Fractional distillation of the crude mixture furnished the two products in pure forms.

Experiment 5: One-Pot Synthesis from Methyl Acrylate

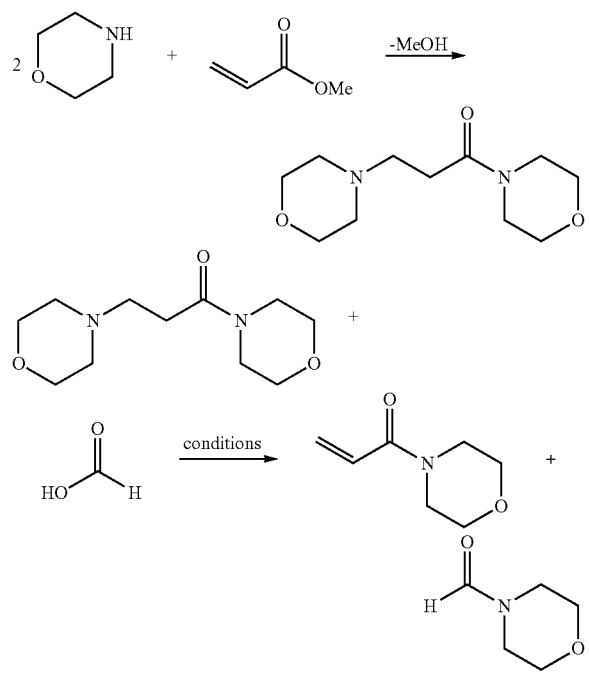

Under Argon atmosphere, a mixture of 92.5 g morpholine and 0.22 g inhibitor BHT was charged into a flask, to which 37.0 g methyl acrylate was slowly added over 1 hr, followed by additional portion of 18.5 g morpholine. The mixture was heated up to 55° C. with stirring for 2 hrs, to which a mixture of 7.8 g 30% MeONa in 40 g MeOH was added over 1 hr. The reaction was brought to 75° C. with stirring for 5 hrs. Upon completion, 2.3 g concentrated $H_2SO_4$ was added. Excess MeOH and morpholine were next sequentially removed under reduced pressure. The formed 93.4 g 1,3-dimorpholinopropan-1-one was directly combined with 18.8 g formic acid, 0.84 g phenothiazine, and 450 mL xylene, and the resultant mixture was further heated up to 140° C. with stirring for 2 hrs, an additional portion of 18.1 g formic acid was added and the stirring was continued overnight. The crude mixture was concentrated under reduced pressure to give 95.6 g crude oil. GC analysis on the sample revealed formation of N-formylmorpholine (46.1%) and ACMO (51.7%). Fractional distillation of the crude mixture furnished the two products in pure forms.

Experiment 6

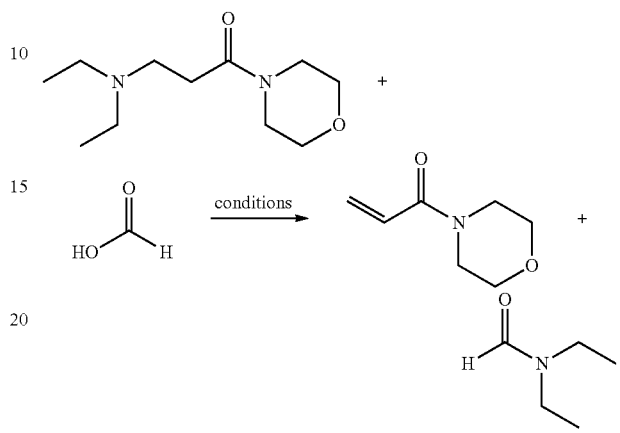

Under argon atmosphere, a mixture of prepared 5.2 g 3-(diethylamino)-1-morpholinopropan-1-one, 1.3 g formic acid, 58 mg phenothiazine, and 25 mL xylene was charged into a flask and further heated up to 140° C. with stirring for 45 mins, an additional portion of 1.2 g formic acid was added and the stirring was continued for 5 hrs. The crude mixture was concentrated under reduced pressure to give 5.1 g crude oil. GC analysis on the sample revealed formation of N,N-diethylformamide (44.8%) and ACMO (50.3%). Fractional distillation of the crude mixture furnished the two products in pure forms.

The present invention has now described in detail, including the preferred embodiments thereof. However, it should be appreciated that those skilled in the art, upon consideration of the present disclosure, may make modifications and/or improvements on this invention that fall within the scope and spirit of the invention.

What is claimed is:
1. A process for preparing compound C and compound D simultaneously, wherein the process is illustrated in equation (I), starting materials are compound A and compound B under conditions:

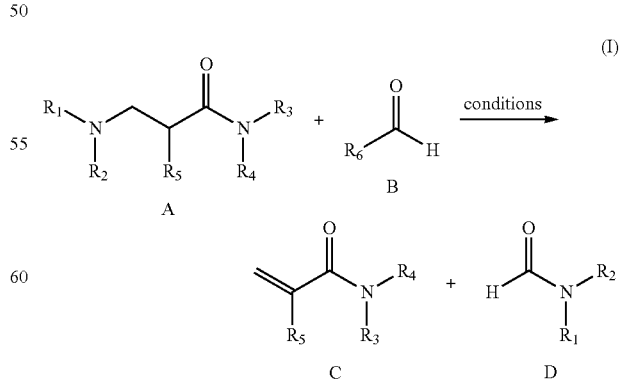

wherein in the equation (I), $R_1$ and $R_2$ is independently selected from the group consisting of hydrogen, linear or branched aliphatic groups containing 1-24 carbons ($C^1$-$C^{24}$) and aromatic groups containing 6-24 carbons ($C^6$-$C^{24}$);

$R_3$ and $R_4$ is independently selected from the group consisting of hydrogen, $C^1$-$C^{24}$ aliphatic groups and $C^6$-$C^{24}$ aromatic groups;

$R_5$ is selected from the group consisting of hydrogen, methyl ($CH_3$) and hydroxymethyl ($CH_2OH$);

$R_6$ is selected from the group consisting of OH, H, CHO, $R_1$, $OR_1$, $NHR_1$, $NR_1R_2$ and OM, wherein M is a metal cation;

the conditions are two or more factors selected from the group consisting of organic base, inorganic base, catalyst, promoter, inhibitor, heat, microwave, ultrasonic wave, vacuum, pressure and solvent.

2. The process according to claim 1, wherein the compound A is prepared by equation (III) with compound E, compound F and compound G as starting compounds

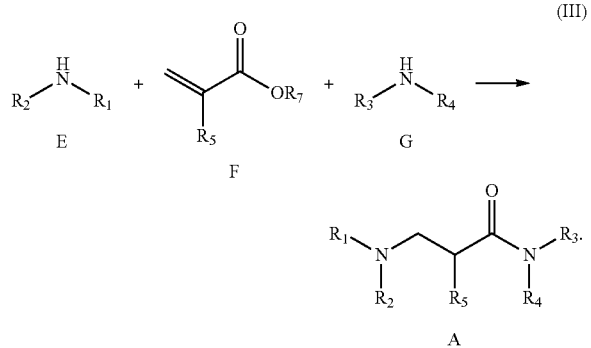

3. The process according to claim 1, wherein the compound B is formic acid that is prepared by the following reaction:

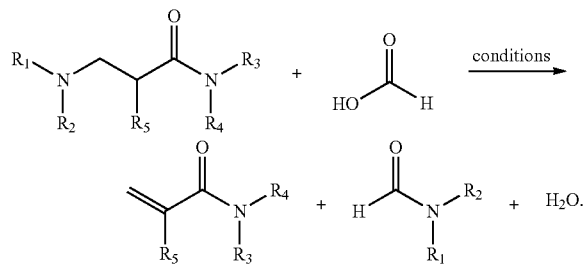

4. The process according to claim 1, wherein the compound B is formaldehyde that is prepared by the following reaction:

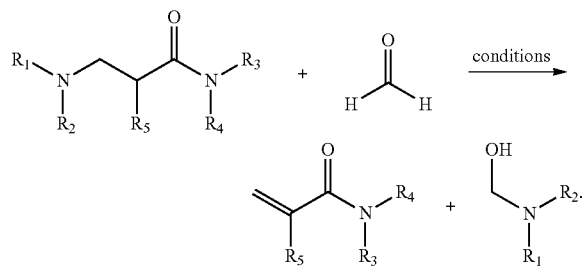

5. The process according to claim 1, wherein the organic base is aliphatic or aromatic amine; the inorganic base is alkaline metal, alkaline-earth metal, or hydroxide, oxide, sulfide, carbonate, carboxylate, sulfonate of transition metal; the catalyst or promoter is Lewis acidic or basic compound.

6. The process according to claim 1, wherein the inhibitor is one or compounds selected from the group consisting of phenol, phenol derivative, hydroquinone, benzoquinone, naphthoquinone, phenothiazine, phosphite, N-nitroso-N-phenylhydroxylamine aluminum salt, 4-hydroxy-2,2,6,6-tetramethyl-piperidinooxy, tri-(4-hydroxy-TEMPO) phosphate, copper chloride and copper dibuthyldithiocarbamate; the amount of the inhibitor employed is in the range of 0.01-5% molar fraction.

7. The process according to claim 6, wherein the phenol derivative is 1,2-benzenediol, 1,3-benzenediol, 1,4-benzenediol, 2,4-dimethyl-6-tert-butylphenol, 2,6-di-tert-butyl-4-methylphenol, 4-methoxyphenol, dibutylhydroquinone, or pyrogallic acid.

8. The process according to claim 6, wherein the amount of inhibitor employed are in the range of 0.01-3% molar fraction.

9. The process according to claim 1, wherein the reaction temperature is in the range of –25-400° C.

10. The process according to claim 2, wherein the reaction temperature is in the range of –25-400° C.

11. The process according to claim 1, wherein the reaction pressure is in the range of 0.001-50 atm.

12. The process according to claim 2, wherein the reaction pressure is in the range of 0.001-50 atm.

13. The process according to claim 1, wherein the solvent is one or more compound selected from a group consisting of aromatic or aliphatic hydrocarbon, halogenated aromatic or aliphatic hydrocarbon, ester, alcohol, ether, nitrile, ketone, amide, sulfone, carbonate, water, super-critical carbon dioxide and ionic liquids.

14. The process according to claim 3, wherein the compound A is 1,3-dimorpholinopropan-1-one, the compound C is 4-acryloylmorpholine, and the compound D is N-formylmorpholine, the corresponding reaction equation is show as following:

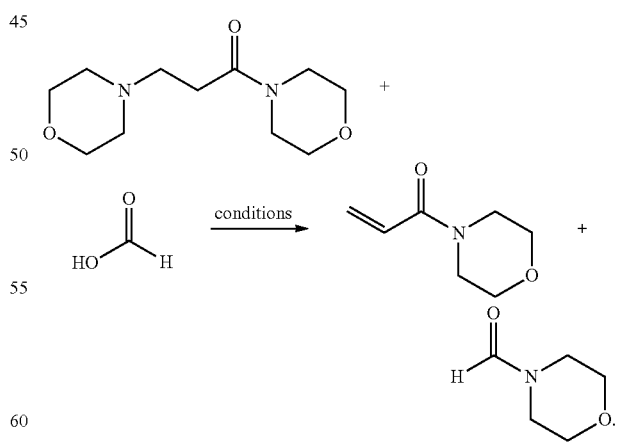

15. The process according to claim 3, the compound A is 3-(diethylamino)-N,N-diethylpropanamide, the compound C is N,N-diethylacrylamide, the compound D is N,N-diethyl formamide, the corresponding reaction equation is show as following:

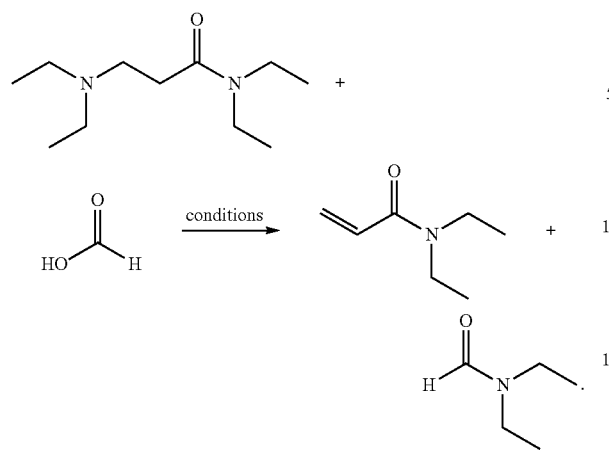
16. The process according to claim 1, wherein the compound C is one of the following structures:
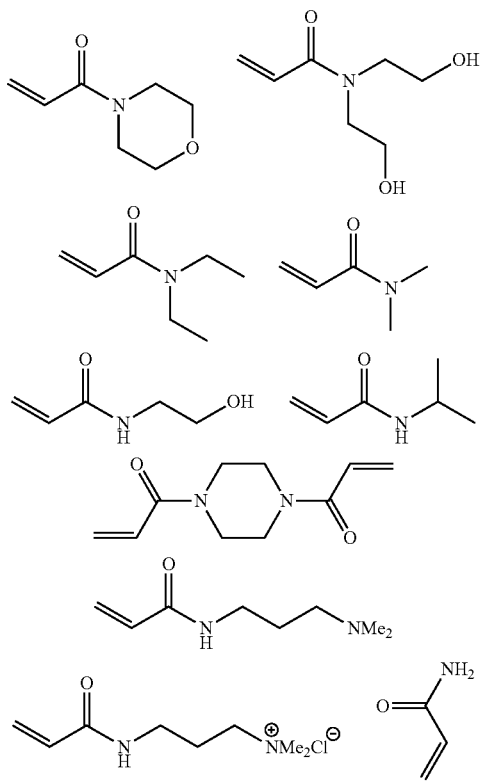
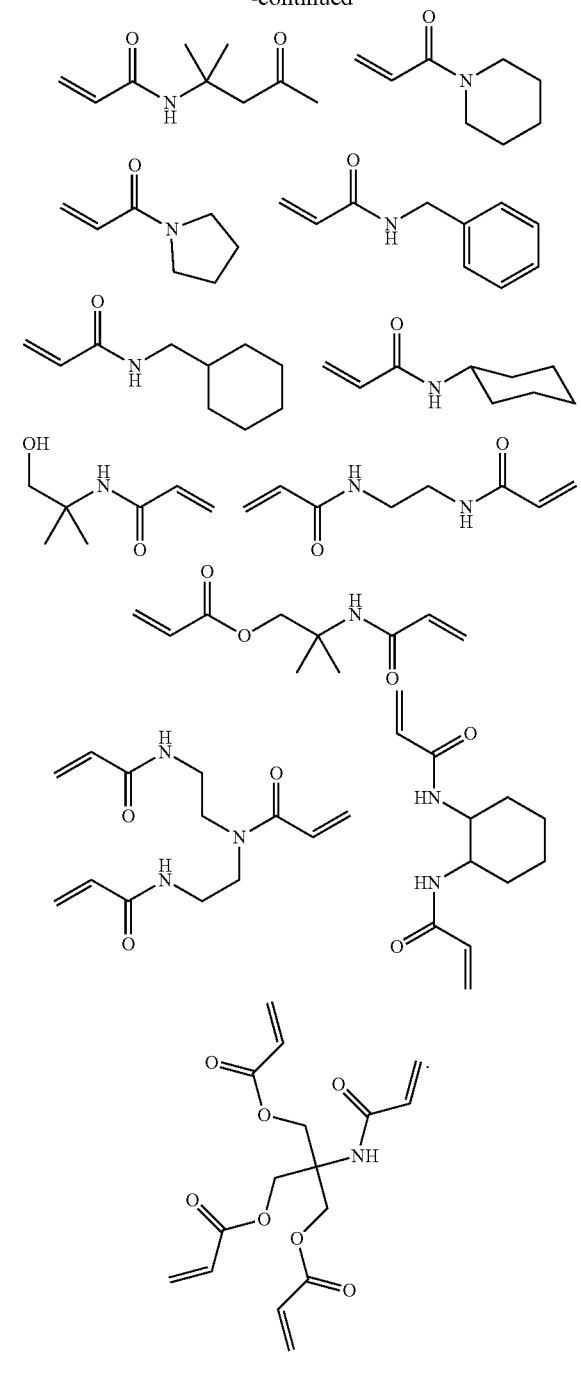
* * * * *